(12) United States Patent  
Roy et al.

(10) Patent No.: US 6,685,958 B2  
(45) Date of Patent: Feb. 3, 2004

(54) QUINOLONE CARBOXYLIC ACID COMPOSITIONS AND RELATED METHODS OF TREATMENT

(75) Inventors: Samir Roy, San Ramon, CA (US); Santosh Kumar Chandrasekaran, Moraga, CA (US); Katsumi Imamori, Chiba (JP); Takemitsu Asaoka, Chiba (JP); Akihiro Shibata, Chiba (JP); Masami Takahashi, Tokyo (JP); Lyle M. Bowman, Pleasanton, CA (US)

(73) Assignees: InSite Vision Incorporated, Alameda, CA (US); SSP Co., Ltd., Tokyo (JP)

( * ) Notice: Subject to any disclaimer, the term of this patent is extended or adjusted under 35 U.S.C. 154(b) by 64 days.

(21) Appl. No.: 09/840,871

(22) Filed: Apr. 25, 2001

(65) Prior Publication Data

US 2002/0187193 A1 Dec. 12, 2002

(51) Int. Cl.[7] .............................. A61F 13/00; A61F 2/00
(52) U.S. Cl. ...................... 424/427; 424/422; 514/212; 514/213; 514/218; 514/219; 514/29; 514/912; 514/954; 514/964; 514/187
(58) Field of Search ................................. 424/422, 427; 514/212, 213, 187, 218, 29, 219, 912, 954, 964

(56) References Cited

U.S. PATENT DOCUMENTS

| | | |
|---|---|---|
| 3,868,445 A | 2/1975 | Ryde et al. |
| 4,551,456 A | 11/1985 | Katz |
| 4,615,697 A | 10/1986 | Robinson |
| 4,692,454 A | 9/1987 | Mich et al. |
| 4,851,415 A | 7/1989 | Mich et al. |
| 5,124,154 A | 6/1992 | Babcock et al. |
| 5,188,826 A | 2/1993 | Chandrasekaran et al. |
| 5,192,535 A | 3/1993 | Davis et al. |
| 5,209,926 A | 5/1993 | Babcock et al. |
| 5,252,319 A | 10/1993 | Babcock et al. |
| 5,256,408 A | 10/1993 | Babcock et al. |
| 5,332,582 A | 7/1994 | Babcock et al. |
| 5,340,572 A | 8/1994 | Patel et al. |
| 5,385,900 A * | 1/1995 | Konno et al. ............... 514/218 |
| 5,430,028 A | 7/1995 | Kaihoh et al. |
| 5,447,926 A | 9/1995 | Konno et al. |
| 5,474,764 A | 12/1995 | Patel et al. |
| 5,538,721 A | 7/1996 | Babcock et al. |
| 5,767,153 A | 6/1998 | Bowman et al. |
| 5,814,655 A | 9/1998 | Patel et al. |
| 5,977,171 A | 11/1999 | Bowman et al. |
| 6,159,458 A | 12/2000 | Bowman et al. |
| 6,239,113 B1 * | 5/2001 | Dawson et al. ............... 514/29 |
| 6,265,444 B1 | 7/2001 | Bowman et al. |
| 6,309,630 B1 | 10/2001 | Patel et al. |
| 6,378,526 B1 | 4/2002 | Bowman et al. |
| 6,397,849 B1 | 6/2002 | Bowman et al. |

FOREIGN PATENT DOCUMENTS

EP      0 142 426       5/1985

OTHER PUBLICATIONS

Davies. Biopharmaceutical considerations in topical ocular drug delivery. Clinical and Experimental Pharmacology & Physiolog (2000), 27, 558–562. 2000.*

Ralf Stahlmann and Hermut Lode, *Safety Overview, Ocular Toxicity*, in The Quinolones, 3rd Edition, pp. 407–408 (Vincent T. Andriole ed., 2000) Academic Press, San Diego.

* cited by examiner

*Primary Examiner*—Thurman K. Page  
*Assistant Examiner*—Lakshmi Channavajjala  
(74) *Attorney, Agent, or Firm*—Arnold & Porter

(57) ABSTRACT

The present invention relates to the use of quinolone carboxylic acid formulations in the treatment of ocular and periocular infections. The present invention also relates to sustained release compositions comprising specific quinolone carboxylic acid compounds. The invention also relates to quinolone carboxylic acid compositions and methods of preparing the same.

37 Claims, 5 Drawing Sheets

SS732

Figure 3. Conjunctival Concentration of SS734 Following Instillation of Various Eyedrop Formulations

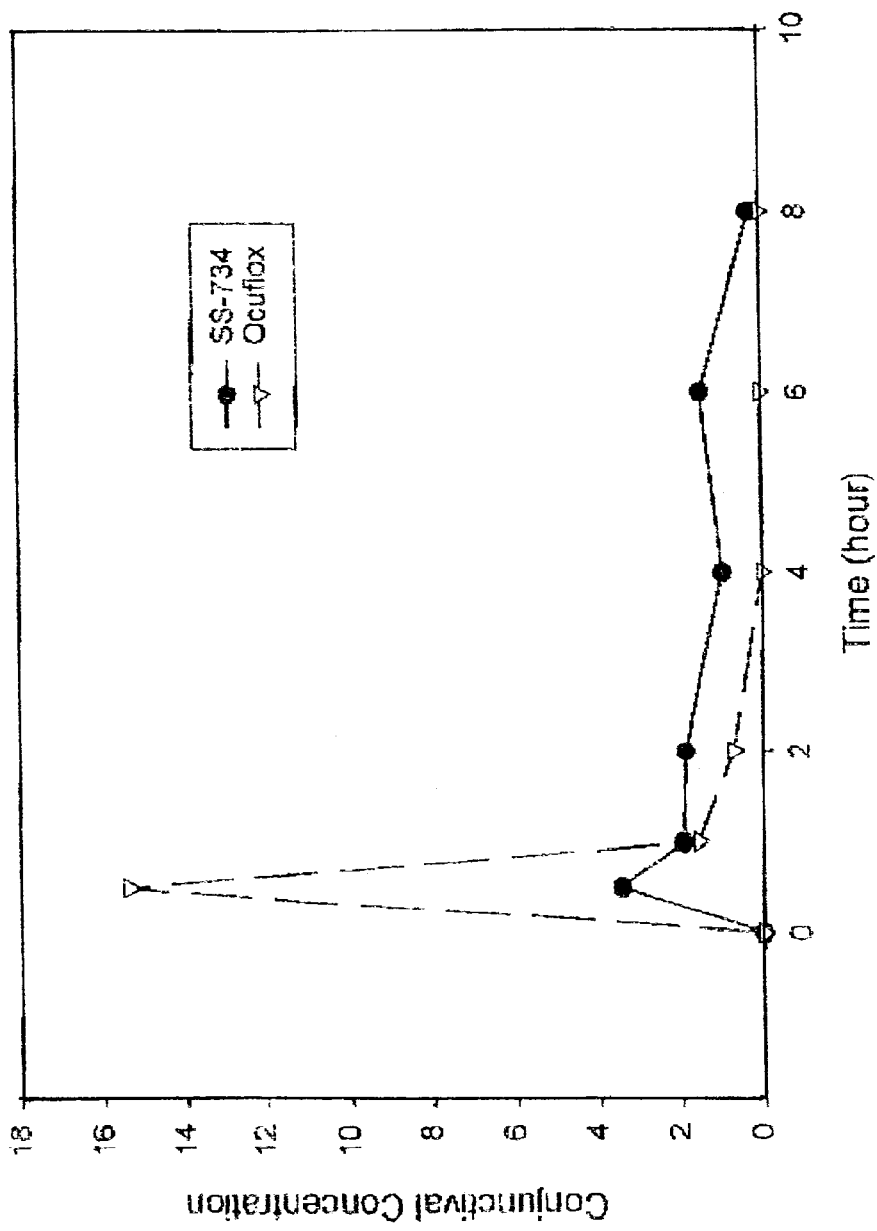
Figure 5. Comparison of the Conjunctival Concentrations of SS734 and Ocuflox

QUINOLONE CARBOXYLIC ACID COMPOSITIONS AND RELATED METHODS OF TREATMENT

FIELD OF THE INVENTION

The present invention relates to the use of quinolone carboxylic acid formulations in the treatment of ocular and periocular infections. The present invention also relates to sustained release compositions comprising specific quinolone carboxylic acid compounds in a vehicle that permits administration in drop form. The invention also relates to quinolone carboxylic acid compositions and methods of preparing the same.

BACKGROUND OF THE INVENTION

Treatment of ocular and periocular infections can be effected by the application of ointments or the instillation of topical antibiotic suspensions to the eye. Such compositions can employ, for example, one or more of the following antibiotic agents: neomycin, polymixin B, bacitracin, trimethoprim, tobramycin, terramycin, sulfacetamide (e.g., CORTICOSPORIN™, Monarch Pharmaceuticals, Bristol, Tenn.; NEODECADRON™, Merck & Co., West Point, Pa.; POLYSPORIN™, Glaxo Wellcome Inc., Research Triangle Park, N.C.; POLYTRIM™ AND BLEPHAMIDE™, Allergan Inc., Irvine, Calif.; TOBRADEX™, Alcon Laboratories, Fortworth, Tex.; TERA-COTRIL™, Pfizer Inc., New York, N.Y. etc.). Compositions such as: CHIBOXIN™ (Merck and Co., West Point, Pa.), CILOXAN™ (Alcon Laboratories, Fortworth, Tex.) and OCUFLOX™ (Allergan Inc., Irvine, Calif.) employ quinolone antimicrobials in aqueous solution or aqueous suspension.

As in the topical administration of other medicaments to the eye, the delivery of antimicrobial agents is influenced by a variety of factors, among them comfort, consistency and accuracy of dosage, type and time of any vision interference, ease of administration, and timing of delivery. These factors have been discussed, for example, in Davis et al., U.S. Pat. No. 5,192,536.

While the art has produced a variety of compositions for the treatment of ocular and periocular infections, there is still a need for broad-spectrum antimicrobial compositions with the characteristics of high bioavailabity and adsorption. Such compositions would be even more desirable provided they comprise a vehicle that readily permits accurate administration of dosages in a convenient form such as drops. It is also desirable that the composition be non-irritating and soothing to already irritated ocular and periocular tissues. The aforementioned compositions are even more desirable when they also provide sustained release of the antimicrobial compositions and are not subject to rapid dilution or rapid removal of the antibiotics by lacrimation.

There is a need in the art for topically applied antimicrobial agents and compositions useful in their administration.

SUMMARY OF THE INVENTION

The present invention includes and provides a topical ophthalmic composition comprising a quinolone carboxylic acid derivative of formula (I),

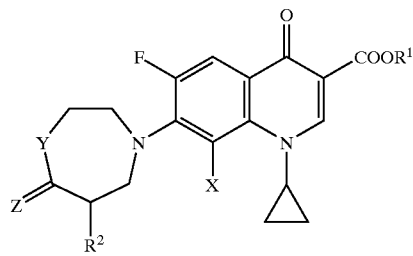

wherein $R^1$ is a hydrogen atom, an alkyl group, an aralkyl group, an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or $N-R^3$, wherein $R^3$ is a hydrogen atom or a lower alkyl group, and Z is an oxygen atom or two hydrogen atoms.

The present invention includes and provides a method of treating or preventing an infection in the ocular or periocular region comprising: delivering to the ocular or periocular region a composition comprising a quinolone carboxylic acid derivative of formula (I),

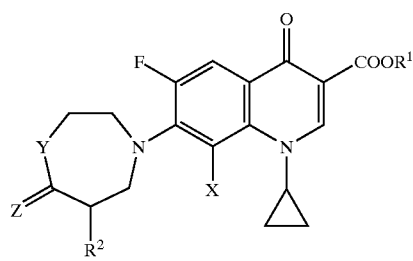

wherein $R^1$ is a hydrogen atom, an alkyl group, an aralkyl group, an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or $N-R^3$, wherein $R^3$ is a hydrogen atom or a lower alkyl group, and Z is an oxygen atom or two hydrogen atoms.

The present invention includes and provides a method of preparing a sustained release topical ophthalmic delivery system, comprising: preparing an composition comprising a quinolone carboxylic acid derivative of formula (I), (I)

$$\text{[structure]}$$

wherein $R^1$ is a hydrogen atom, an alkyl group, an aralkyl group, an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or $N-R^3$, wherein $R^3$ is a hydrogen atom or a lower alkyl group, and Z is an oxygen atom or two hydrogen atoms; and, packaging said composition for administration to the eye.

BRIEF DESCRIPTION OF THE FIGURES

FIG. 5 is a line graph showing conjunctival concentration of (R)-(+)-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid over time compared to the conjunctival concentration of the quinolone antibiotic in OCUFLOX™ after a single dose administration of each composition.

DETAILED DESCRIPTION OF THE INVENTION

Figure 1B:
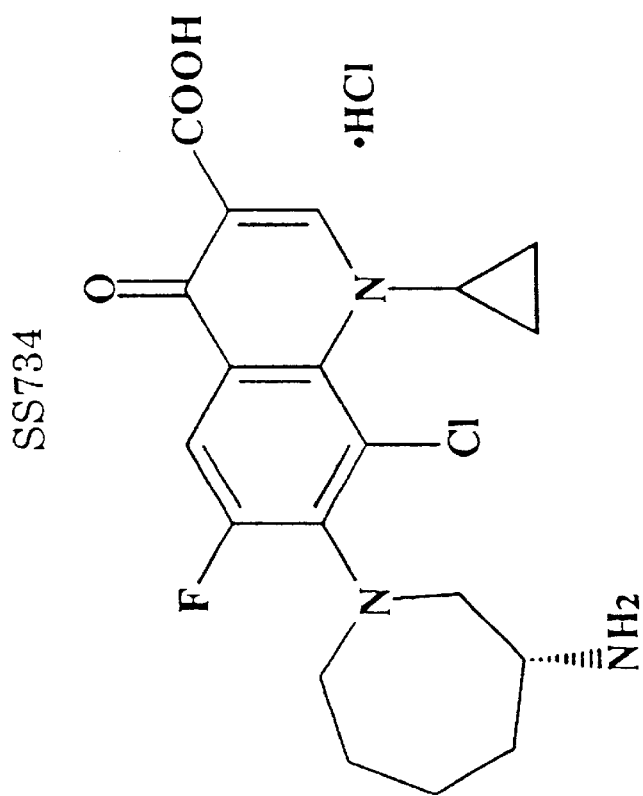
FIG. 1b shows the structure of (R)-+-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid, which is referred to herein as SS734.

The present invention includes and provides compositions for the treatment of ocular infections comprising broad-spectrum quinolone antimicrobials in the form of ointments or instillants, such as solutions and suspensions, as are known in the art, for application to the ocular and periocular region. Other embodiments of the present invention include compositions for ocular and periocular administration comprising a vehicle that permits administration at a suitable initial viscosity, which then substantially increases upon contact with tissues or fluids because the tissues or fluids raise the pH of the administered composition.

In a preferred embodiment, the quinolone carboxylic acid antimicrobial agent is a compound having formula (I),

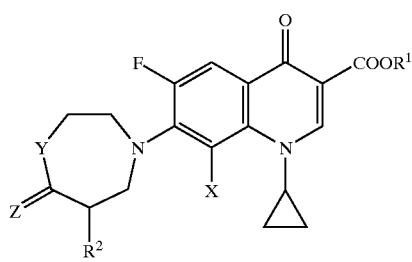

(I)

wherein $R^1$ is a hydrogen atom, an alkyl group, an aralkyl group, or an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or N—$R^3$, wherein $R^3$ is a hydrogen atom or a lower alkyl group, and Z is an oxygen atom or two hydrogen atoms.

Specific examples of groups represented by $R^1$ in formula (I) include, without limitation: linear or branched alkyl groups having 1–12 carbon atoms; aralkyl groups (e.g., benzyl, phenyl ethyl, methyl benzyl, naphtyl methyl, etc.) and ester residual groups which can be hydrolyzed in vivo, or upon exposure to the tissues or fluids of a living body, including the tissues and tear fluid of the ocular and periocular region (e.g., a alkanoyloxyalkyl, alkoxycarbonyloxyalkyl, carbamoylalkyl, alkoxyalkyl, and the like; specifically, acetoxymethyl, 1-acetoxyethyl, ethoxycarbonyloxymethyl, carbamoylmethyl, carbamoylethyl, methoxymethyl, methoxyethyl etc.).

Specific examples of amino groups that may be substituted by one or two lower alkyl groups, represented by $R^2$, include, without limitation: amino, methylamino, ethylamino, isopropylamino, dimethylamino, diethylamino, and diisopropylamino. When $R^2$ in formula (I) is not hydrogen, the carbon atom to which $R^2$ is bonded is asymmetrical, which gives rise to optical isomers, R and S, for compounds of formula (I). The sustained release formulations of the present invention include formulations employing either optical isomer separately or in combination, including the racemate.

Specific examples of halogen atoms represented by X include, without limitation: chlorine, fluorine, bromine, iodine, and the like.

Lower alkyl groups may be linear or branched alkyl groups having 1–5 carbon atoms, (e.g., methyl, ethyl, i-propyl, sec-butyl, t-butyl, amyl, etc.).

The preparation and use of quinolone carboxylic acids of formula (I) as antimicrobial agents are disclosed by Konno et al. in U.S. Pat. No. 5,385,900 and U.S. Pat. No. 5,447,926.

Formulation of the instant invention may also advantageously employ salts of compounds of formula (I). As examples of useful salts of compounds of formula (I), salts of alkali metal, inorganic acid, organic acid, and the like are given. More specific examples include: lithium salts, sodium salts, potassium salts, and the like, as salts of alkali metal; hydrochloride, sulfate, nitrate, hydrobromide, phosphate, and the like, as salts of inorganic acids; and acetate, fumarate, maleate, lactate, citrate, tartarate, malate, oxalate, methanesulfonate, benzenesulfonate, p-toluenesulfonate, and the like, as salts of organic acid.

The preparation of quinolone carboxylic acids of formula (I) agents are described by Konno et al. in U.S. Pat. No. 5,385,900 and U.S. Pat. No. 5,447,926.

In a preferred embodiment, the quinolone carboxylic acid is (R)-(+)-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid, as shown in FIG. 1b.

Figure 1A:
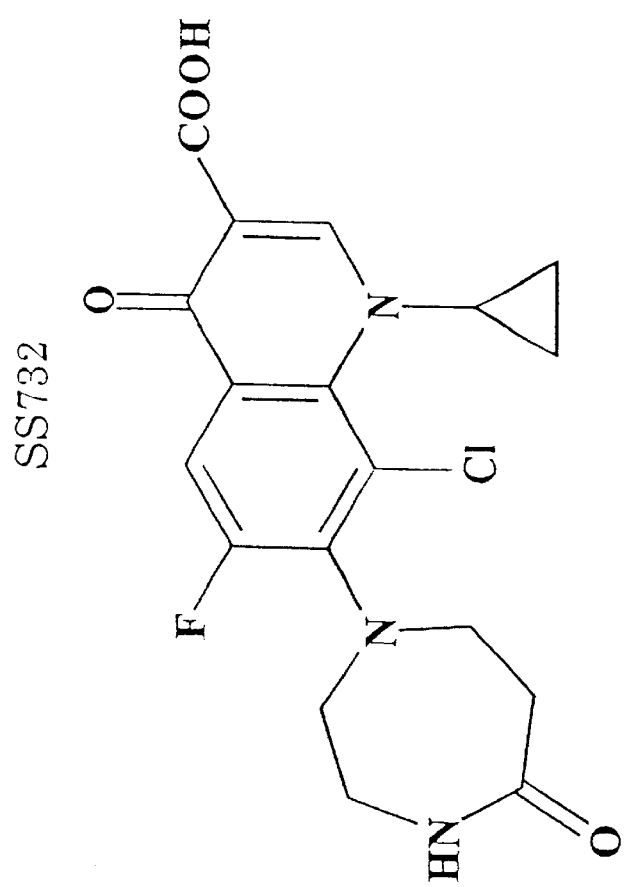
FIG. 1a shows the structure of quinolone antimicrobials 8-chloro-1-cyclopropyl-6-fluoro-7-(2,3,4,5,6,7-hexahydro-5-oxo-1H-1,4-diazepin-1-yl)-1,4-dihydro-4-oxoquinoline-3-carboxylic acid, which is referred to herein as SS732.

In another preferred embodiment, the quinolone carboxylic acid is 8-chloro-1-cyclopropyl-6-fluoro-7-(2,3,4,5,6,7-hexahydro-5-oxo-1H-1,4-diazepin-1-yl)-1,4-dihydro-4-oxoquinoline-3-carboxylic acid, as shown in FIG. 1a.

The quinolone carboxylic acid antimicrobials of the present invention can be incorporated in any of the formulations of this invention, including solutions and suspensions, in therapeutically active amounts, comparable to amounts administered in other dosage forms. These amounts range from about 0.005% to about 10% by weight, and preferably from about 0.007% to about 5%, and even more preferably from 0.02% to 2.5% by weight, based on the total weight of the formulation. In other embodiments the quinolone carboxylic acid antimicrobials can be present from about 0.1% to about 0.5% by weight, from about 0.5% to about 1.0% by weight, from about 2.0% to about 3.0% by weight, or from about 3.0 to about 5.0% by weight, based upon the total weight of the composition. In one embodiment, from about 0.01% to about 1% by weight of quinolone antibiotics of formula (I) can be administered in this manner.

Any composition suitable capable of delivering the quinolone antibiotics of the present invention to the eye can be employed, including solutions and suspensions, which are generally well known in the art. In one embodiment of the present invention, the quinolone carboxylic acid antimicrobial agents described herein are in solution in a composition. In another embodiment, the quinolone carboxylic acid antimicrobial agents of the present invention are in solution and suspension in a composition. In still yet another embodiment of the present invention, a solubilizer is included in a composition to increase the amount of quinolone carboxylic acid antimicrobial agent in solution. Any suitable solubilizer for ophthalmic compositions can be used, including, but not limited to, cyclodextrans. In a preferred embodiment, a composition of the present invention comprises hydroxypropyl-β-cyclodextran. In a preferred embodiment of the present invention, hydroxypropyl-β-cyclodextran is about 1.0% to about 30.0%, and more preferably from about 5.0% to about 20.0% by weight of said composition, based on the total weight of said composition.

In one embodiment, the vehicles useful for ocular and periocular administration of quinolone antimicrobials of formula (I), at a suitable initial viscosity which then substantially increases in viscosity upon contact with tear fluid, are described in Davis et al. U.S. Pat. No. 5,192,535. Ocular administration vehicles, such as those set forth in Davis et al., comprise lightly crosslinked polymers of acrylic acid or the like which are, in general, well known in the art. In a preferred embodiment, such polymers are prepared from at least about 50%, more preferably at least about 60%, more preferably at least about 70%, more preferably at least about 80%, more preferably least about 90%, and even more preferably from about 95% to about 99.9% by weight, based on the total weight of monomers present, of one or more carboxyl-containing monoethylenically unsaturated monomer. In a preferred embodiment, acrylic acid is used as a carboxyl-containing monoethylenically unsaturated monomer. In a further embodiment, unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to, or instead of acrylic acid.

Preferred vehicles that employ lightly crosslinked polymers can be crosslinked by using a small percentage, i.e., less than about 5%, such as from about 0.5% or from about 0.1% to about 5%, and preferably from about 0.2% to about 1%, based on the total weight of monomers present, of a polyfunctional crosslinking agent. In another embodiment, the instant invention also contemplates the use of lightly crosslinked polymers crosslinked with from about 0.01% to about 0.05%, from about 0.06% to about 0.1%, from about 0.11% to about 0.5%, from about 0.55% to about 1.0%, from about 1.5% to about 2.5%, from about 2.6% to about 3.5%, or from about 3.6% to about 4.5%, of crosslinking agent in by weight, based on the total weight of the monomers present. Included among such crosslinking agents are non-polyalkenyl polyether difunctional crosslinking monomers such as: divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. A preferred crosslinking agent is divinyl glycol. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalxyl acrylate or methacrylate reaction products, and reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250.

It is possible to prepare lightly crosslinked polymers employing one or more carboxyl-containing monomers as the only monomers present, together with a crosslinking agent or agents. In one embodiment, lightly crosslinked polymers can be polymers in which up to about 1%, 2%, 5%, 10%, 15%, 20%, 30% or 40% by weight, of the carboxyl-containing monoethylenically unsaturated monomer or monomers have been replaced by one or more non-carboxyl-containing monoethylenically unsaturated monomers containing only physiologically and ophthalmologically innocuous substituents. Non-carboxyl-containing monoethylenically unsaturated monomers may be present in any range from 0% to about 40% by weight of the monomers present, and are preferably present from about 0% to about 20% by weight. Non-carboxyl-containing monoethylenically unsaturated monomers useful in preparing the polymers include: acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like; vinyl acetate, N-vinylpyrrolidone, and the like; see Mueller et al. U.S. Pat. No. 4,548,990, for a listing of additional monoethylenically unsaturated monomers that can be used in compositions of the present invention. Particularly preferred polymers are lightly crosslinked acrylic acid polymers wherein the crosslinking monomer is 2,3-dihydroxyhexa-1, 5-diene or 2,3-dimethylhexa-1,5-diene.

It is preferable to prepare lightly crosslinked polymers that can be used in conjunction with the vehicles of this invention by suspension or emulsion polymerizing the monomers, using conventional free radical polymerization catalysts, to a dry particle size of not more than about 30 μm in equivalent spherical diameter. In a preferred embodiment the dry particle size ranges from about 1 to about 30 μm, and preferably from about 3 to about 20 μm, in equivalent spherical diameter. In one embodiment, such polymers are estimated to range in molecular weight (in daltons) from 1 to 10 billion and preferably about 2–5 billion.

The relationship between the degree of crosslinking and particle size is significant for the lightly crosslinked polymers of the vehicles that increase in viscosity upon administration. As the particles are present in a suspension, the degree of crosslinking is necessarily at a level such as to avoid substantial dissolution of the polymer. As the polymers undergo rapid gelation in response to the pH change resulting from contact with tear fluid, the degree of crosslinking is necessarily not so great that gelation is precluded. The increased gelation occurs with a change in the pH of the formulation upon contact with tear fluid. As will be appreciated by those in the art, the formulations of the invention, which are designed to increase in viscosity subsequent to administration, can be delivered at a pH of from about 3 to about 6.5 and an osmotic pressure of from about 10 to about 400 mOsM. As will be appreciated, tear fluid is at a higher pH of about 7.2 to about 7.4. With the pH increase, carboxylic acid (COOH) undergoes a sodium replacement (to COONa), and the sodium form disassociates, causing the polymer to expand. If the polymer particle size is too large, induced swelling can tend to take up voids in the volume between large particles that are in contact with one another, rather than cause gelation.

If the polymer employed in vehicles designed to undergo increases in viscosity subsequent to administration were in a dissolved state, as it would be if there were insufficient crosslinking because of a too low of a ratio of crosslinker to monomer, particle size would be less relevant. In a suspension, however, particle size can be relevant to comfort. In a preferred system of the present invention, the small particle size and light crosslinking synergistically yield rapid gelation of the administered composition upon exposure to tear fluid, which increases the pH of the composition. In various embodiments the present invention includes and provides for the use of particles less than about 30 $\mu$m, less than about 20 $\mu$m, less than about 10 $\mu$m, or less than about 6 $\mu$m. Particle size below 30 $\mu$m is preferred in obtaining the increased viscosity. Moreover, at the 30 $\mu$m size and below, eye comfort is improved.

Aqueous suspensions containing polymer particles prepared by suspension or emulsion polymerization whose average dry particle size is appreciably larger than about 30 $\mu$m in equivalent spherical diameter are less comfortable when administered to the eye than suspensions otherwise identical in composition containing polymer particles whose equivalent spherical diameters are, on the average, below about 30 $\mu$m. It has also been discovered that lightly crosslinked polymers of acrylic acid or the like prepared to a dry particle size appreciably larger than about 30 $\mu$m in equivalent spherical diameter and then reduced in size, e.g., by mechanically milling or grinding, to a dry particle size of not more than about 30 $\mu$m in equivalent spherical diameter do not work as well as polymers made from aqueous suspensions.

Without wishing to be bound by any theory or mechanism advanced to explain the functioning of this invention, one possible explanation for the difference of such mechanically milled or ground polymer particles as the sole particulate polymer present is that grinding disrupts the spatial geometry or configuration of the larger than 30 $\mu$m lightly cross-linked polymer particles, perhaps by removing uncrosslinked branches from polymer chains, by producing particles having sharp edges or protrusions, or by producing particles having ordinarily too broad a range of particle sizes to afford satisfactory delivery system performance. A broad distribution of particle sizes can impair the viscosity-gelation relationship of the more preferred embodiments. In any event, such mechanically reduced particles are less easily hydratable in aqueous suspension than particles prepared to the appropriate size by suspension or emulsion polymerization, and also are less able to gel in the eye under the influence of tear fluid to a sufficient extent, and are less comfortable once gelled than gels produced in the eye using the aqueous suspensions of this invention. However, up to about 5%, more preferably 10%, 15%, 20%, 30%, or more preferably 40%, by weight, based on the total weight of lightly crosslinked particles present, of such milled or ground polymer particles can be admixed with solution or emulsion polymerized polymer particles having dry particle diameters of not more than about 30 $\mu$m when practicing this invention. Such mixtures will also provide satisfactory viscosity levels in the ophthalmic medicament delivery systems and in the in situ gels formed in the eye coupled with ease and comfort of administration and satisfactory sustained release of the medicament to the eye, particularly when such milled or ground polymer particles, in dry form, average from about 0.01 to about 30 $\mu$m, preferably from about 0.05 to about 15 $\mu$m, more preferably from about 0.25 to about 7.5 $\mu$m, and most preferably from about 1 to about 5 $\mu$m, in equivalent spherical diameter. In other embodiments, milled or ground polymer particles, in dry form, averaging from about 5.0 to about 10 $\mu$m, or milled or ground particles averaging from about 10 to about 20 $\mu$m, or milled or ground particles averaging from about 20 to about 30 $\mu$m, can be admixed with solution or emulsion polymerized polymer particles having dry particle diameters of not more than about 30 $\mu$m.

In the most preferred embodiments of the invention, the vehicles employed in the formulations comprise particles having a narrow particle size distribution within a 10 $\mu$m band of major particle size distribution which contains at least 80%, more preferably at least 90%, and most preferably at least 95% of the particles. Also, there is no more than 20%, preferably no more than 10%, and most preferably no more than 5% particles of fines (i.e., particles having a particle size below 1 $\mu$m). The presence of large amounts of such fines has been found to inhibit the desired gelation upon eye contact. In addition, the use of a monodispersion of particles will give maximum viscosity and an increased eye residence time of the ophthalmic medicament delivery systems for a given particle size. Monodispersed particles having a particle size of 30 $\mu$m and below are most preferred. It is also preferred that as the average particle size is lowered from 30 $\mu$m to lower sizes such as 6 $\mu$m, that the band of major particle size distribution be also narrowed (for example to 5 $\mu$m). Preferred sizes for particles within the band of major particle distribution are less than about 30 $\mu$m, more preferably less than about 20 $\mu$m and most preferably from about 1 $\mu$m to about 5 $\mu$m. Good particle packing is aided by a narrow particle size distribution.

Preferred formulations of this invention will contain amounts of lightly crosslinked polymer particles ranging from about 0.1% to about 6.5% by weight, more preferably from about 0.5% to about 4.5% and even more preferably from about 1.0% to about 3.0% by weight, based on the total weight of the suspension. In other embodiments the formulations of this invention may contain amounts of lightly crosslinked polymer particles ranging from about 0.1% to about 6.5% by weight, or 0.25% to about 4.0% by weight, or preferably about 0.5% to about 1% by weight, based on the total weight of the suspension. The formulations can preferably be prepared using pure, sterile water, preferably deionized or distilled, having no physiologically or ophthalmologically harmful constituents, and can be adjusted to any desirable pH, and preferably below about 6.5 with ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases. In a preferred embodiment, the polymer is a carboxy containing polymer. In a another preferred embodiment, the polymer is a cross-linked carboxy containing polymer.

When formulating the aqueous suspensions of this invention, their osmotic pressure ($\pi$) will be adjusted to from about 10 milliosmolar (mOsM) to about 400 mOsM, and preferably from about 100 to about 250 mOsM, using appropriate amounts of physiologically and ophthalmologically acceptable salts. Sodium chloride is preferred to approximate physiologic fluid, and amounts of sodium chloride ranging from about 0.01% to about 1% by weight, and preferably from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate and the like can also be used in addition to or instead of sodium chloride to achieve osmolalities within the above-stated ranges.

When preparing compositions comprising the lightly crosslinked polymer particles, the amounts of lightly crosslinked polymer particles, the pH, and the osmotic pressure chosen from within the above-stated ranges can be correlated with each other and with the degree of crosslinking to give aqueous suspensions with desired visocities, preferably having viscosities ranging from about 500 to about 10,000, more preferably from 1,000 to about 5,000, 1500 to 3500, and even more preferably from 2000 to 3000 centipoise, as measured at a shear rate of 2.25 sec$^{-1}$ using a Brookfield Digital LV-CP viscometer equipped with a CP-40 spindle at 25° C. (Brookfield Engineering Laboratories Inc.; Middleboro, Mass.). At viscosities greater than 5000 cps, the handling and administration of the composition via an eye dropper can become unnecessarily cumbersome and error prone. At viscosities less than 1000 cps, the composition may be too easily washed from the eye by tearing and the like and may not have enough residence time in the eye. Also, because the viscosity is predominantly a function of the kind and amount of crosslinked carboxy-containing polymer (as a function of pH), the amount of crosslinked carboxy-containing polymer present at such a low viscosity is generally too low to provide the desired release profile of medicament.

The viscous gels that result from fluid eyedrop formulations delivered by means of the aqueous suspensions of the more preferred embodiments of this invention have residence times in the eye ranging from about 2 to about 12 hours, e.g., from about 3 to about 6 hours. The quinolone carboxylic acids contained in these formulations will be released from the gels at rates that depend on such factors as the drug itself and its physical form, the extent of drug loading and the pH of the system, as well as on any drug delivery adjuvants, such as ion exchange resins compatible with the ocular surface, which may also be present. For the fluoroquinolone antimicrobial SS734, which is shown in FIG. 1b, for example, release in the rabbit eye is in excess of four hours, as measured by the conjunctival and tear fluid concentrations of SS734 (see FIGS. 3 and 4, for example).

Pro-drug containing counterparts of the inventive formulations are also within the scope of the present invention. One may for example employ pro-drug formulations of quinolone antimicrobials of formula (I), wherein R1 is an ester residual group that can be hydrolyzed in vivo. Hydrolysis of pro-drugs in vivo is specifically intended to include the hydrolysis of pro-drugs of the quinolone antimicrobials of formula (I) in the ocular and periocular regions. The R1 group of such pro-drug containing formulations could be selected from alkanoyloxyalkyl, alkoxycarbonyloxyalkyl, carbamoylalkyl, alkoxyalkyl, and the like; more specifically, acetoxymethyl, 1-acetoxyethyl, ethoxycarbonyloxymethyl, carbamoylmethyl, carbamoylethyl, methoxymethyl and methoxyethyl.

Formulations of this invention may also contain excipients, such as ophthalmologically acceptable pH adjusting acids, bases, or buffers. Additional excipients may include, for example without limitation, chelating agents (e.g., ETDA etc), surfactants and additional polymeric agents (e.g., block copolymer of ethylene oxide and propylene oxide, such as Poloxamer™ polymers) and preservatives. Those skilled in the art will be able to readily appreciate that diverse excipients, such as those set forth in "Remington's Pharmaceutical Sciences," Mack Publishing Co., Easton, Pa., can be incorporated into the compositions of this invention.

The aqueous topical ophthalmic medicament delivery compositions of this invention can be prepared in any of several ways. For example a convenient method involves adding the drug and other formulation components to about 95 percent of the final water volume and stirring for a sufficient time to dissolve the components or saturate the solution. Solution saturation can be determined in a known manner, e.g., using a spectrophotometer. The pH and concentration of the composition are then adjusted to their final values.

The preparation of compositions containing lightly crosslinked polymers can be achieved in a variety of ways, for example, the lightly crosslinked polymer particles, and the osmolality-adjusting salt can be preblended in dry form, added to all or part of the water, and stirred vigorously until apparent polymer dispersion is complete, as evidenced by the absence of visible polymer aggregates. The antibiotics of the invention can be introduced by addition in dry form to the preblended dry materials, prior to their addition to water. Alternatively, the quinolone antibiotics can be added to the aqueous dispersion in dry form, as a suspension or predissolved (in solution) as the dispersion is stirred. Sufficient pH adjusting agent is subsequently added incrementally to reach the desired pH, and more water to reach 100 percent formula weight can be added at this time, if necessary.

In an alternative method of preparing formulations of the invention bearing lightly crosslinked polymeric particles, the lightly crosslinked polymer particles and the osmolality-adjusting salt are first blended in dry form and then added to an antibiotic saturated suspension and stirred until apparent polymer hydration is complete. Following the incremental addition of sufficient pH adjusting agent to reach the desired pH, the remainder of the water is added, with stirring, to bring the suspension to 100 percent formula weight. Yet another method by which to prepare the formulation is to separately prepare a solution comprising the desired quinolone antimicrobial and a suspension comprising the carboxyl-containing particles. The quinolone antimicrobial solution can be prepared in about one third portion of the vehicle solvent (typically water) at a pH at which it is fully soluble and the suspension comprising the carboxyl-containing particles can be prepared in about one third portion of vehicle solvent. After the carboxyl-containing particles have fully hydrated, the solution of quinolone antimicrobial and the suspension of particles are mixed together with stirring and the addition of sufficient base or acid as required to maintain the pH in the desired range. After mixing is complete water is added to 100 percent formula.

Formulations of the invention can be packaged in preservative-free, single-dose non-reclosable containers. In a preferred method, the formulations are prepared and packaged at a desired viscosity, from about 1,000 to about 30,000 centipoise, for administration to the eye in drop form. This permits a single dose of the medicament to be delivered to the eye one drop at a time, with the container discarded after use. Such containers eliminate the potential for preservative-related irritation and sensitization of the corneal epithelium, as has been observed to occur particularly from ophthalmic medicaments containing mercurial preservatives. Multiple-dose containers can also be used, if desired, particularly since the relatively low viscosities of the aqueous suspensions of this invention permit constant, accurate dosages to be administered dropwise to the eye as many times each day as necessary. In those suspensions where preservatives are to be included, suitable preservatives are chlorobutanol, Polyquat, benzalkonium chloride, cetyl bromide, sodium perborate, chlorhexadine, and the like.

As formulations of the invention comprise quinolone antimicrobials active against a broad variety of microorganisms, they are useful in the treatment of infections and associated conditions affecting the ocular and periocular regions associated with the spectrum of microorganisms susceptible to the action of the quinolone antimicrobials. Formulations of the invention are useful in the treating infections of Gram negative and Gram positive bacteria and also in the treatment of mixed infections of Gram negative and Gram positive bacteria including infections of the following Gram negative organisms: *Escherichia coli, Salmonella typhi, Shigella flexneri, Klebsiellia pneumonia, Proteus vulgaris, Proteus rettgeri, Haemophilus influenzae, Pseudomonas aeruginosia, Serratia marcescens, Moraxella morganii, Moraxella lacunata* and *Moraxella catarrhalis*, and infections of the following Gram positive microorganisms: *Bacillus subtilis, Staphylococcus aureus* (including methicillin resistant and susceptible strains), *Staphylococcus epidermidis, Staphylococcus haemolyticus, Staphylococcus hominis, Staphylococcus pyogenes, Streptococcus pneumoniae, Enterococcus faecalis* and *Micrococcus lysodeikticus*. Formulations of the invention are particularly useful in the treatment of ocular and periocular infections of *Streptococcus pneumoniae, Staphylococcus aureus* (including methicillin resistant and susceptible strains), *Haemophilus influenzae, Pseudomonas aeruginosia, Moraxella morganii, Moraxella lacunata Moraxella catarrhalis,* or mixed infections thereof. In a preferred embodiment, formulations of the invention are useful for treatment of an infection of a bacteria selected from the group consisting of *Escherichia coli, Salmonella typhi, Shigella flexneri, Klebsiellia pneumonia, Proteus vulgaris, Proteus rettgeri, Haemophilus influenzae, Pseudomonas aeruginosia, Serratia marcescens, Moraxella morganii, Moraxella lacunata, Moraxella catarrhalis, Bacillus subtilis, Staphylococcus aureus, Staphylococcus epidermidis, Staphylococcus haemolyticus, Staphylococcus hominis, Staphylococcus pyogenes, Streptococcus pneumoniae, Enterococcus faecalis, Micrococcus lysodeikticus* and combinations thereof.

For the purpose of this invention, ocular and periocular regions are defined as the eye and tissues immediately adjacent to the eye, particularly those regions which are exposed to the fluid secretions of the lachrymal apparatus. These include the eyelid, cornea, sclera, conjuntiva, lachrymal apparatus and lachrymal ducts. As will be obvious to those skilled in the art, injury and infection may expose or involve surrounding or underlying tissues in the ocular and periocular region tissues, such as the conjunctival tissues, that may also be advantageously treated using the formulations of the invention.

Treatment of ocular or periocular microbial infections and conditions associated with microbial infections comprises instillation of a sufficient amount of the antibiotic formulation (i.e., a sufficient volume of the formulation to deliver sufficient antibiotic to achieve an antimicrobial effect). In a more preferred embodiment the method of treatment utilizes a relatively low viscosity form of the formulation (i.e., one of suitable viscosity to be readily delivered in drop form which undergoes an increase in viscosity upon contact with the tear fluid and tissues of the ocular or periocular region) to deliver a therapeutically effective dose (a dose sufficient to effect an antimicrobial effect in a subject) of the quinolone antimicrobial agent. Upon contact with the tissues or fluids of the ocular and periocular region, the formulation undergoes an increase in viscosity to a highly viscous form capable of sustained delivery of the quinolone antimicrobials useful in the treatment of ocular infections. Examples of specific conditions that may be treated with the formulation of the invention include: conjunctivitis associated with *Haemophilus influenzae, Staphylococcus aureus, Staphylococcus epidermidis, Streptococcus pneumoniae, Moraxella morganii, Moraxella lacunata,* and *Moraxella catarrhalis* infections, corneal ulcers associated with *Pseudomonas aeruginosia, Serratia marcescens, Staphylococcus aureus, Staphylococcus epidermidis, Streptococcus pneumoniae, Moraxella morganii, Moraxella lacunata,* and *Moraxella catarrhalis* infections and keratitis associated with corneal infections associated with organisms sensitive to the quinolone antibiotics of formula (I). Treatments employing the formulations of this invention are additionally intended to include prophylactic use of the formulations.

In one embodiment of the present invention, the compositions are sustained release formulations for ocular and periocular administration comprising a quinolone in a vehicle that permits administration at a suitable initial viscosity, which increases to a viscosity greater than that of the form administered upon contact with tear fluid or tissues of the ocular and periocular region. Among the advantages of such formulations are the ability to provide for a sustained release of the quinolone antimicrobial agents and the ability to deliver higher levels of quinolone antimicrobials to the ocular and periocular regions as compared to the short duration release and levels of quinolone antimicrobials that can be achieved with simple aqueous solutions or suspensions of quinolone antimicrobials. Other advantages of the instant invention include the ability to effectively treat a broad spectrum of Gram negative, Gram positive or mixed infections of Gram negative and Gram positive bacterial infections using fewer administrations of the antimicrobial agent. This has advantages to both physicians and patients as it increases the ability of the physician to prescribe an effective treatment at the earliest time a patient is seen, rather than waiting until sensitivity in culture is determined. In addition, as sustained release formulations of the invention require fewer administrations the level of patient compliance is more likely to be high, thereby resulting in more positive outcomes from treatment.

Compositions of this invention are advantageous in their presentation of quinolone carboxylic acids to the tissues of the ocular and periocular regions for numerous reasons. First the formulations of this invention permit the presentation of unexpectedly high levels of quinolone antibiotics to the ocular and periocular region. In one embodiment, when employing sustained release compositions and compositions that increase in viscosity upon application to the tissues of the ocular and periocular regions, the levels of quinolone antimicrobials obtained are superior to those that can be achieved with other conventional eyedrops that do not increase in viscosity upon administration and contact with lachrymal secretions, the eye, or the tissues surrounding the eye. Second, the formulations of this invention permit the release of quinolone antibiotic compounds over an unexpectedly prolonged time period, thereby reducing requirement for frequent repeated dosing. Third, as the quinolone antibiotics of formula I have increased absorption they display an increased bioavailiblity in the tissues of the eye and around the eye. Fourth, the quinolone antibiotics of formula I display an increased potency against gram positive organisms (e.g., *S. aureus*) while retaining a high level of efficacy against gram negative organisms. This results in the ability to employ the formulation of this invention in the treatment of a broad spectrum of infections and in mixed gram positive and gram negative infections. Because the quinolone antibiotic formulations of the present invention comprise broad spectrum antibiotics, they permit physicians dealing with ocular and periocular infections to prescribe an effective treatment at the earliest time a patient is seen, rather than waiting until sensitivity in culture is determined. In addition, as the formulations of the invention provide sustained release of the quinolone antimicrobials, they require fewer administrations. Hence, the level of patient compliance is more likely to be high, resulting in more positive outcomes from treatment. For at least the forgoing reasons, the formulations and methods of treatment of the instant invention represent a significant advance in the treatment of ocular and periocular infections.

In order that those skilled in the art can more fully appreciate aspects of this invention, the following examples are set forth. These examples are given solely for purposes of illustration, and should not be considered limiting.

EXAMPLE I

An exemplary formulation of the quinolone antimicrobial SS734 is shown in this example. Table I summarizes an exemplary formulation comprising the quinolone antimicrobial SS734 according to the invention, and two comparison formulations containing SS734. All components are given as their weight percent of a 100 ml solution (i.e., grams/100 ml), except for NaOH and water. NaOH is added to yield a final pH of about 5.5 to about 5.8 and water is added to yield a final volume of 100 ml. Noveon AA-1™ is the trade name of polymers of acrylic acid crosslinked with divinyl glycol and is a product of B. F. Goodrich; Cleveland, Ohio. Poloxamer™ 407 is a block copolymer of ethylene oxide and propylene oxide manufactured by the BASF Company; Ludwigshafen, Germany. Hydroxypropyl-β-cyclodextrin has been abbreviated as HBPC.

TABLE 1

| Formulation ID | A | B | C |
|---|---|---|---|
| Noveon AA-1 | 0.8 | Not Added | 0.8 |
| HPBC | 5.0 | Not Added | Not Added |

TABLE 1-continued

| Formulation ID | A | B | C |
|---|---|---|---|
| SS734 | 0.3 | 0.3 | 0.3 |
| EDTA | 0.1 | 0.1 | 0.1 |
| NaCl | 0.4 | 0.4 | 0.4 |
| Mannitol | 1.0 | 1.0 | 1.0 |
| Benzalkonium chloride | 0.01 | 0.01 | 0.01 |
| Poloxamer 407 | 0.1 | 0.1 | 0.1 |
| NaOH to a final pH of: | 5.5–5.8 | 5.5–5.8 | 5.5–5.8 |
| Water to a final volume of: | 100 ml | 100 ml | 100 ml |

The formulations are prepared by addition of a separately prepared drug solubilizer solution/suspension to a mixture containing hydrated Noveon, when present, and the remaining excipients with continuous stirring. The resulting composite mixtures are titrated to a final pH of 5.5–5.8, and the final formulation weight of SS734 is adjusted by addition of water to each formulation. Formulations are filled in glass vials, capped, and crimped. Formulation A is a clear solution, with the quinolone antimicrobial completely dissolved. Formulations B and C are suspensions. The solubility fraction of the drug in these suspensions is about 0.3%.

EXAMPLE II

Figure 2:
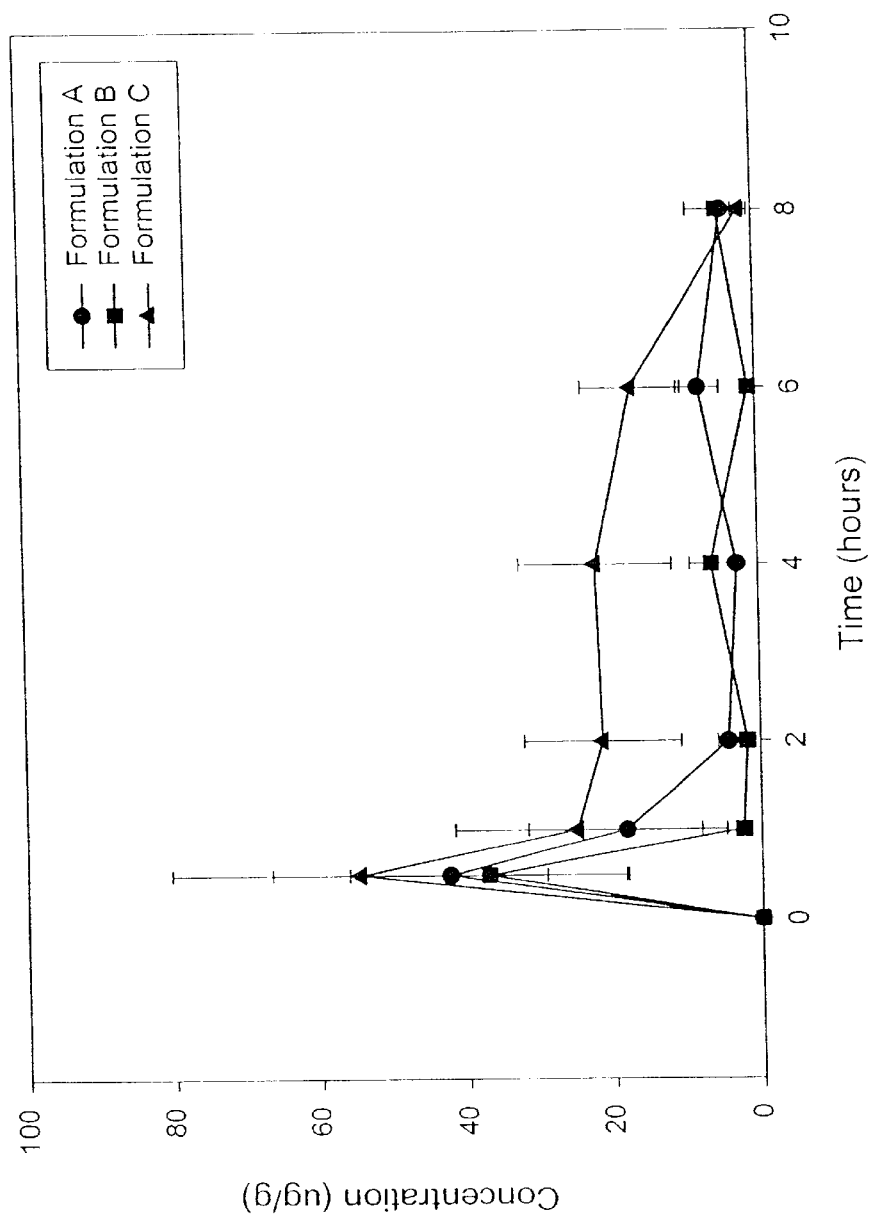
FIG. 2 is a line graph showing tear fluid concentration of (R)-(+)-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid over time following the instillation of three different topical eyedrop formulations containing the compound.

In this example, ocular administration studies with SS734 are performed. For tear fluid concentration studies formulations A, B and C are prepared according to Example I. Following an initial measurement, 25 µl aliquots of the respective formulations are instilled into the eyes of New Zealand white rabbits. The concentration of compound SS734 in tear fluid is measured at the desired subsequent time points. Quantitation of SS734 concentration in tear fluid is conducted employing LCMS for the analysis. Results are shown in FIG. 2.

Figure 3:
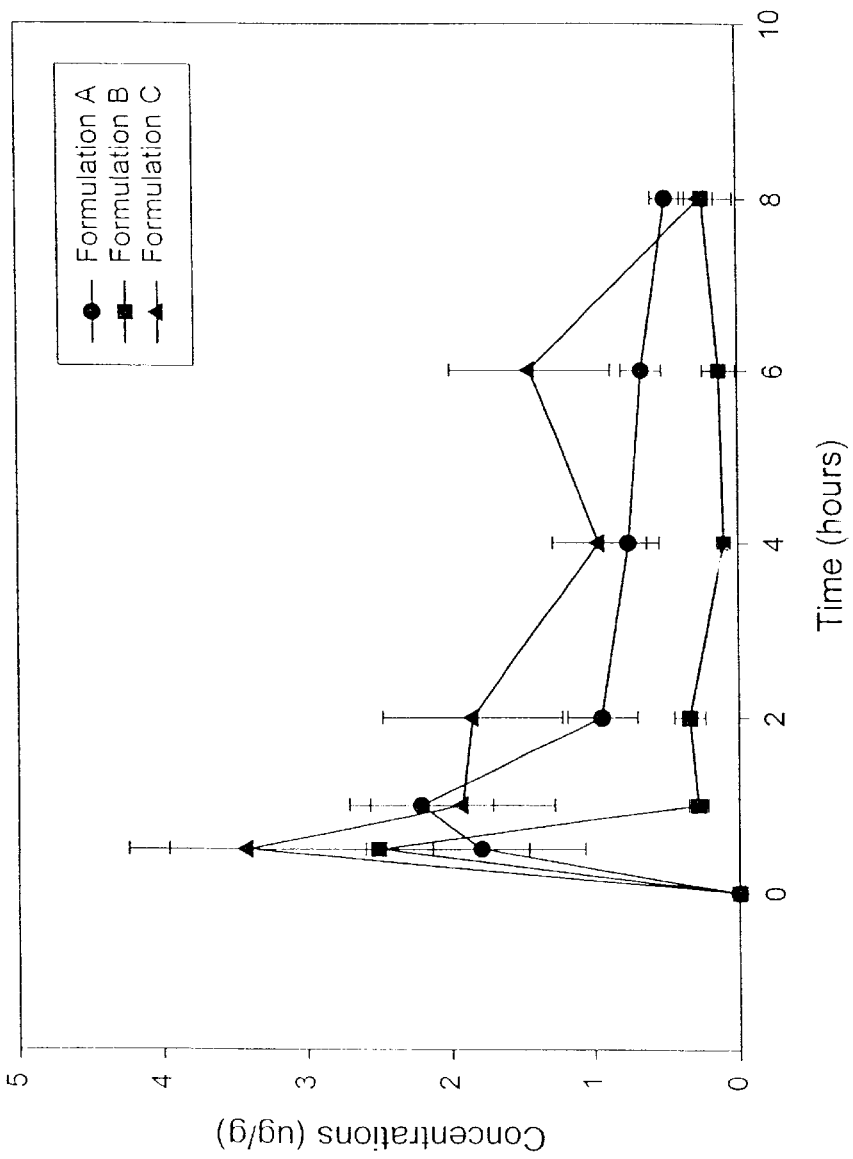
FIG. 3 is a line graph showing conjunctival concentration of (R)-(+)-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid following the instillation of three different eyedrop formulations containing the compound.

For conjunctival concentration studies, formulations A, B, and C are prepared according to Example I, except that each sample contains 0.192% citric acid, which is used to dissolve the SS734 in acidic conditions. Following an initial measurement, 25 µl aliquots of the respective formulations are instilled into the eyes of New Zealand white rabbits. The concentration of compound SS734 available to conjunctival tissue is measured at the desired subsequent time points. Quantitation of SS734 concentration in samples is conducted employing the HPLC system described in Example II. Results are shown in FIG. 3.

The results demonstrate that the inventive formulations according to one of the preferred embodiments of the invention, formulation C, provide extended release of compound SS734 based upon both conjunctival and tear fluid measurements.

EXAMPLE III

Figure 4:
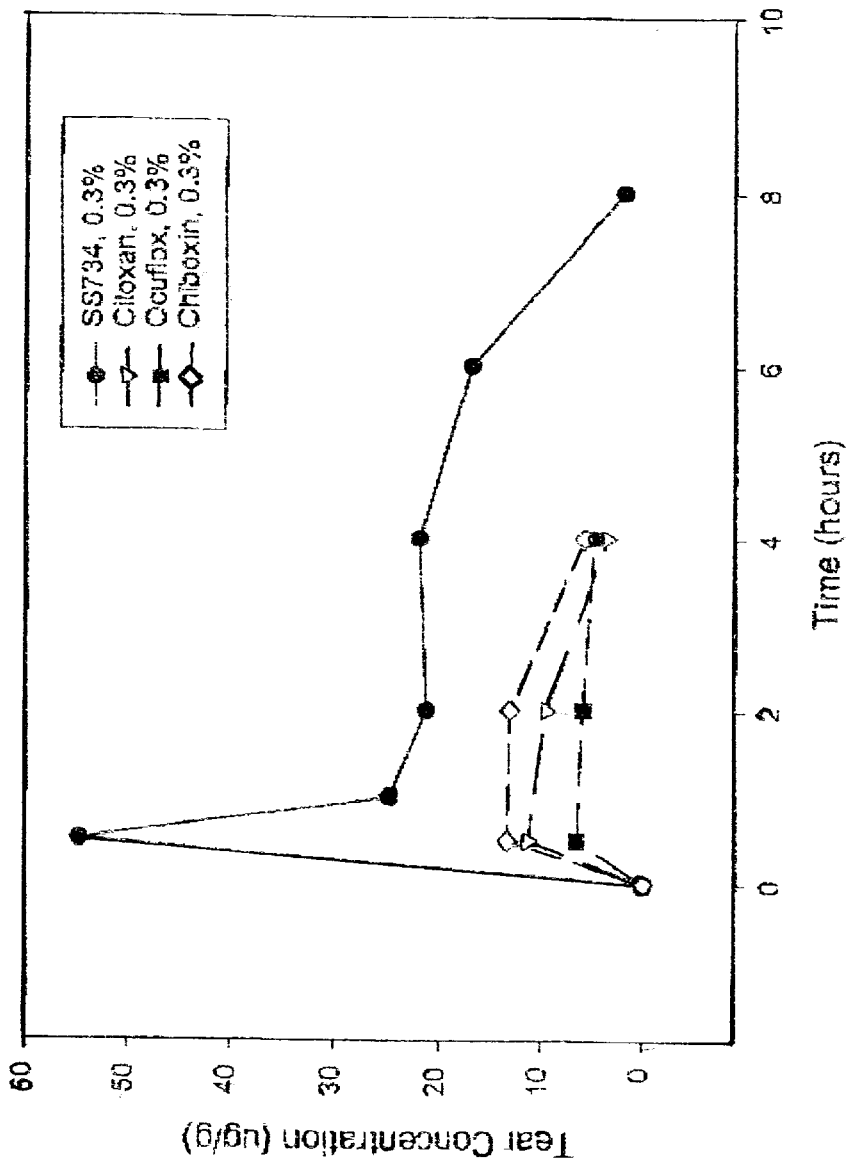
FIG. 4 is a line graph showing tear fluid concentration of (R)-(+)-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid over time compared to the tear fluid concentration of the quinolone antibiotics CILOXAN™, OCUFLOX™ and CHIBOXIN™ as published in the International Journal of Therapeutics, 35(5) 1997, pages 214–217.

In this example, formulation SS734 of the present invention is compared to the published results of several known compounds. Results are shown in FIGS. 4 and 5.

The above discussion of this invention is directed primarily to certain embodiments of the invention. It will be apparent to those of skill in the art that further changes and modifications can be made in the actual implementation of the concepts described herein without departing from the spirit of the invention as defined in the following claims.

Each patent, journal article, or other reference herein cited is herein incorporated by reference in its entirety.

What is claimed is:

1. A topical ophthalmic broad spectrum antibiotic composition comprising: from about 0.005% to about 10% by weight, based upon the total weight of the composition, of a quinolone carboxylic acid derivative of formula (I),

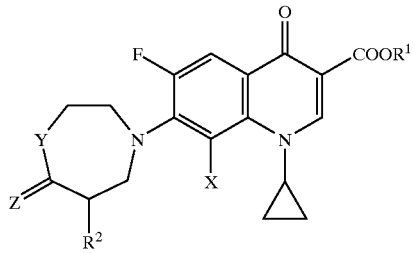

wherein $R^1$ is a hydrogen atom, an alkyl group, an aralkyl group, an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or N—$R^3$, wherein $R^3$ is a hydrogen atom or a lower alkyl group, and Z is an oxygen atom or two hydrogen atoms; and a carboxy containing polymer; wherein said topical ophthalmic broad spectrum antibiotic composition is nonirritating to ocular tissue.

2. The composition of claim 1, wherein said broad spectrum antibiotic composition provides sustained release of said quinolone carboxylic acid derivative.

3. The composition of claim 1, consisting essentially of a quinolone carboxylic acid derivative of formula (I), wherein $R^1$ is a hydrogen atom, an alkyl group, an aralkyl group, an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or N—$R^3$, wherein $R^3$ is a hydrogen atom or a lower alkyl group, and Z is an oxygen atom or two hydrogen atoms; and a carboxy containing polymer.

4. The composition of claim 1, wherein said carboxy containing polymer comprises from about 0.1% to about 6.5% by weight of said composition, based on the total weight of said composition.

5. The composition of claim 4, wherein said polymer contains up to about 40% by weight of non-carboxyl containing monoethylenically unsaturated monomers.

6. The composition of claim 1, wherein said quinolone carboxylic acid derivative of formula (I) is present from about 0.02%–0.25% by weight based upon the total weight of the composition.

7. The composition as in claim 1, further comprising one or more excipients.

8. The composition as in claim 1, in which said quinolone carboxylic acid derivative of formula (I) is a pro-drug form of said quinolone carboxylic acid derivative.

9. The composition as in claim 1, wherein said quinolone carboxylic acid derivative of formula (I) is the free acid (R)-(+)-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid, a salt thereof, or hydrochloride thereof.

10. The composition as in claim 1, wherein said quinolone carboxylic acid derivative of formula (I) is the free acid 8-chloro-1-cyclopropyl-6-fluoro-7-(2,3,4,5,6,7-hexahydro-5-oxo-1H-1,4-diazepin-1-yl)-1,4-dihydro-4-oxoquinoline-3-carboxylic acid, a salt thereof, or hydrochloride thereof.

11. The composition of claim 1, further comprising a solubilizer.

12. The composition of claim 11, wherein said solubilizer is hydroxypropyl-β-cyclodextrin.

13. The composition of claim 12, wherein said hydroxypropyl-β-cyclodextrin is about 5.0% to about 20.0% by weight of said composition, based on the total weight of said composition.

14. The composition of claim 1, further comprising a cross-linked carboxy containing polymer.

15. The composition of claim 14, wherein said cross-linked carboxy containing polymer comprises from about 0.1% to about 6.5% by weight of said composition, based on the total weight of said composition.

16. The composition of claim 15, wherein said cross-linked carboxy containing polymer comprises from about 0.5% to about 1.0% by weight of said composition, based on the total weight of said composition.

17. A method of treating or preventing a bacterial infection in the ocular or periocular region comprising:
delivering to the ocular or periocular region a topical ophthalmic broad spectrum antibiotic composition comprising from about 0.005% to about 10% by weight, based upon the total weight of the composition, of a quinolone carboxylic acid derivative of formula (I),

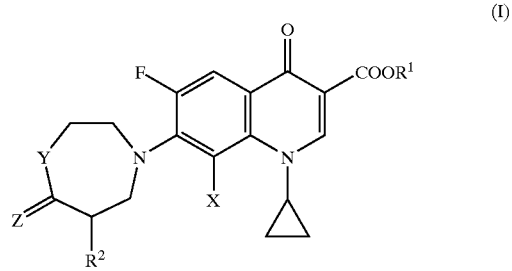

wherein $R^1$ is a hydrogen atom, an alkyl group, an aralkyl group, an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or N—$R^3$, wherein $R^3$ is a hydrogen atom or a lower alkyl group, and Z is an oxygen atom or two hydrogen atoms; wherein said topical ophthalmic broad spectrum antibiotic composition is nonirritating to ocular tissue.

18. The method of claim 17, wherein said broad spectrum antibiotic composition provides sustained release of said quinolone carboxylic acid derivative.

19. The method of claim 17, wherein said broad spectrum antibiotic composition further comprises a carboxy containing polymer.

20. The method of claim 19, wherein said carboxy containing polymer comprises from about 0.1% to about 6.5% by weight of said composition, based on the total weight of said composition.

21. The method of claim 20, wherein said polymer contains up to about 40% by weight of non-carboxyl containing monoethylenically unsaturated monomers.

22. The method of claim 17, wherein said quinolone carboxylic acid derivative of formula (I) is present from about 0.02%–2.5% by weight based upon the total weight of the composition.

23. The method of claim 17, wherein said broad spectrum antibiotic composition further comprises one or more excipients.

24. The method as in claim 17, in which said quinolone carboxylic acid derivative of formula (I) is a pro-drug form of said quinolone carboxylic acid derivative.

25. The method as in claim 17, wherein said quinolone carboxylic acid derivative of formula (I) is the free acid (R)-(+)-7-(3-amino-2,3,4,5,6,7-hexahydro-1H-azepin-1-yl)-8-chloro-1-cyclopropyl-6-fluoro-1,4-dihydro-4-oxoquinoline-3-carboxylic acid, a salt thereof, or hydrochloride thereof.

26. The method as in claim 17, wherein said quinolone carboxylic acid derivative of formula (I) is the free acid 8-chloro-1-cyclopropyl-6-fluoro-7-(2,3,4,5,6,7-hexahydro-5-oxo-1H-1-1,4-diazepin-1-yl)-1,4-dihydro-4-oxoquinoline-3-carboxylic acid, a salt thereof, or hydrochloride thereof.

27. The method of claim 17, wherein said broad spectrum antibiotic composition further comprises a solubilizer.

28. The method of claim 27, wherein said solubilizer is hydroxypropyl-β-cyclodextrin.

29. The method of claim 28, wherein said hydroxypropyl-β-cyclodextrin is about 5.0% to about 20.0% by weight of said composition, based on the total weight of said composition.

30. The method of claim 17, wherein said broad spectrum antibiotic composition further comprises a cross-linked carboxy containing polymer.

31. The method of claim 30, wherein said cross-linked carboxy containing polymer comprises from about 0.1% to about 6.5% by weight of said composition, based on the total weight of said composition.

32. The method of claim 30, wherein said cross-linked carboxy containing polymer comprises from about 0.5% to about 1.0% by weight of said composition, based on the total weight of said composition.

33. The method as in claim 17, wherein said broad spectrum antibiotic composition is a solution, composition, ointment, or instillant.

34. The method as in claim 17, wherein said infection is an infection of Gram positive bacteria, Gram negative bacteria, or a mixed infection of Gram positive and Gram negative bacteria.

35. The method as in claim 34, wherein said infection is an infection of a bacteria selected from the group consisting of *Escherichia coli, Salmonella typhi, Shigella flexneri, Klebsiellia pneumonia, Proteus vulgaris, Proteus rettgeri, Haemophilus influenzae, Pseudomonas aeruginosia, Serratia marcescens, Moraxella morganii, Moraxella lacunata, Moraxella catarrhalis, Bacillus subtilis, Staphylococcus aureus, Staphylococcus epidermidis, Staphylococcus haemolyticus, Staphylococcus hominis, Staphylococcus pyogenes, Streptococcus pneumoniae, Enterococcus faecalis, Micrococcus lysodeikticus,* and combinations thereof.

36. The method of claim 32, wherein the infection is a mixed infection of Gram negative bacteria and Gram positive bacteria.

37. A method of preparing a sustained release topical ophthalmic delivery system, comprising:

preparing a topical ophthalmic broad spectrum antibiotic composition comprising from about 0.005% to about 10% by weight, based upon the total weight of the composition, of a quinolone carboxylic acid derivative of formula (I),

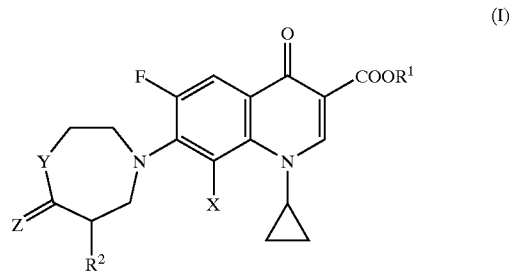

(I)

wherein $R^1$ is a hydrogen atom, an alkyl group, an aralkyl group, an ester residual group which can be hydrolyzed in vivo, $R^2$ is a hydrogen atom or an amino group which may be substituted by one or two lower alkyl groups, X is a hydrogen atom or a halogen atom, Y is $CH_2$, O, S, SO, $SO_2$, or N—$R^3$, wherein $R^3$ is a hydrogen atom or a lower alkyl group, and Z is an oxygen atom or two hydrogen atoms; and, packaging said composition for administration to the eye; wherein said topical ophthalmic broad spectrum antibiotic composition is nonirritating to ocular tissue.

* * * * *